United States Patent
Klingenbeck

(10) Patent No.: US 8,630,468 B2
(45) Date of Patent: Jan. 14, 2014

(54) IMAGING METHOD FOR THE REPRESENTATION OF THE RESULTS OF INTRAVASCULAR IMAGING AND CFD RESULTS AND MEDICAL SYSTEM FOR EXECUTION OF THE METHOD

(75) Inventor: Klaus Klingenbeck, Aufseβ (DE)

(73) Assignee: Siemens Aktiengesellschaft, Munich (DE)

( * ) Notice: Subject to any disclaimer, the term of this patent is extended or adjusted under 35 U.S.C. 154(b) by 405 days.

(21) Appl. No.: 13/100,546

(22) Filed: May 4, 2011

(65) Prior Publication Data

US 2011/0274323 A1    Nov. 10, 2011

(30) Foreign Application Priority Data

May 5, 2010    (DE) .......................... 10 2010 019 421

(51) Int. Cl.
*G06K 9/00* (2006.01)

(52) U.S. Cl.
USPC ........................................................ 382/128

(58) Field of Classification Search
USPC ................................................ 382/128, 154
See application file for complete search history.

(56) References Cited

U.S. PATENT DOCUMENTS

| | | | |
|---|---|---|---|
| 7,500,784 B2 | 3/2009 | Grebner | |
| 7,657,299 B2 * | 2/2010 | Huizenga et al. | 600/410 |
| 2006/0058647 A1 | 3/2006 | Eichler et al. | |
| 2007/0123771 A1 * | 5/2007 | Redel et al. | 600/407 |
| 2007/0223794 A1 * | 9/2007 | Preiss et al. | 382/128 |
| 2008/0228086 A1 | 9/2008 | Costa et al. | |
| 2008/0312673 A1 | 12/2008 | Drury et al. | |

FOREIGN PATENT DOCUMENTS

| | | |
|---|---|---|
| DE | 19827460 A1 | 12/1998 |
| DE | 102008014792 B3 | 6/2009 |

OTHER PUBLICATIONS

David A. Steinman et al.; "Image-Based Computational Simulation of Flow Dynamics in a Giant Intracranial Aneurysm"; AJNR Am J Neuroradiol 24: pp. 559-566, Apr. 2003.
Kharboutly et al.; "Arterio-Venous Fistula: Two Cases Realistic Numerical Blood Flow Simulations"; Proceedings of the 29th Annual International Conference of the IEEE EMBS Cité Internationale, Lyon, France, Aug. 23-26, 2007 pp. 2980-2983.

* cited by examiner

*Primary Examiner* — Tom Y Lu

(57) ABSTRACT

An imaging method for representing results of intravascular imaging (IVB) and CFD results of plaques of a vascular vessel tree of a patient and an imaging medical system for execution of the method are proposed. A 3-D image data set of the area under examination is acquired with x-ray beams for the generation of 3-D x-ray images. A 3-D reconstruction image of the area under examination is generated from the 3-D x-ray images. IVB images are generated by intravascular imaging. Larger calcified plaques in the 3-D x-ray images and IVB images are identified for determining orientation points or landmarks. The spatial position of the plaques are correlated and/or registered based on the orientation points or landmarks. The IVB image data and 3-D image data are fused and reproduced.

13 Claims, 4 Drawing Sheets

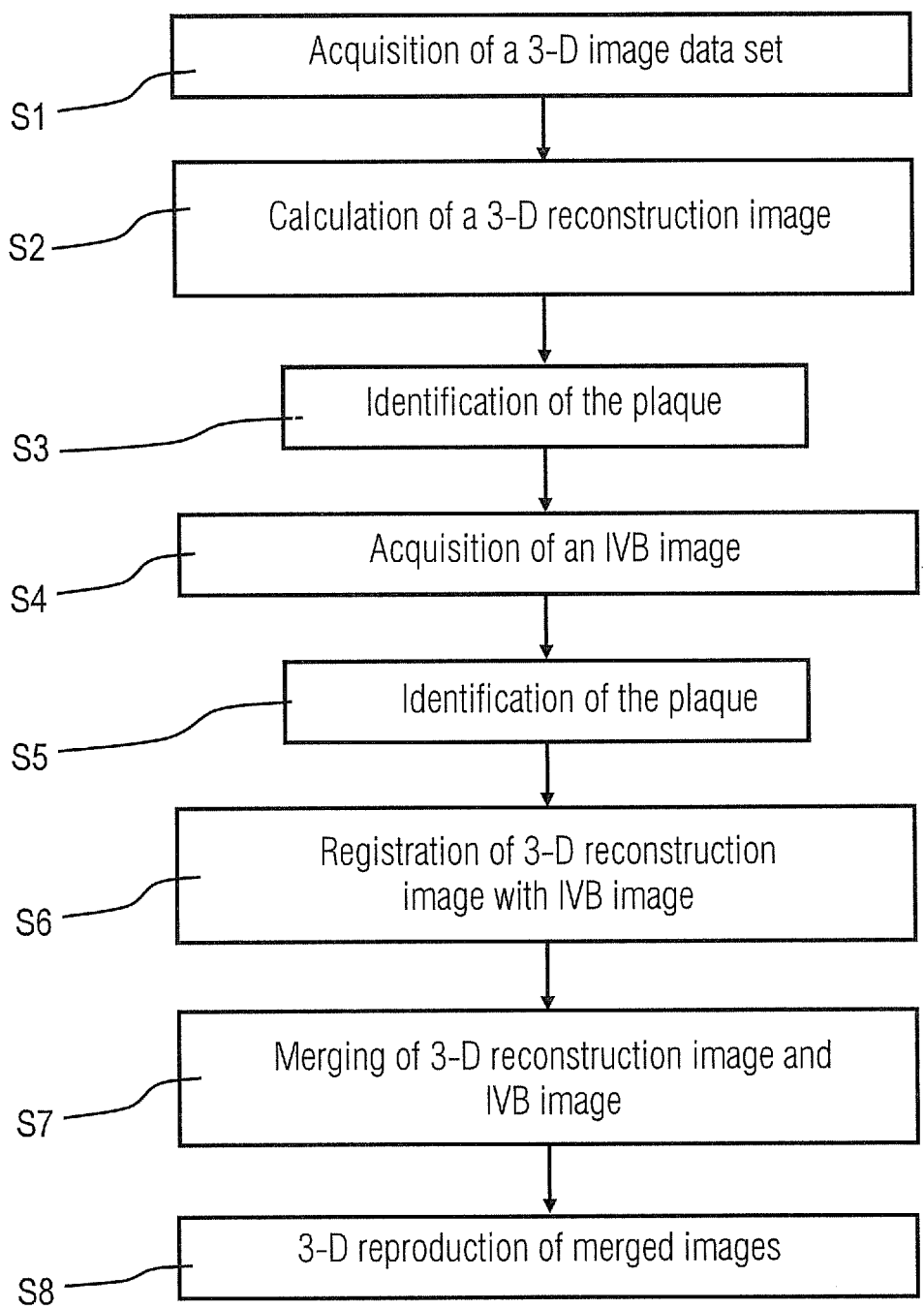

US 8,630,468 B2

IMAGING METHOD FOR THE REPRESENTATION OF THE RESULTS OF INTRAVASCULAR IMAGING AND CFD RESULTS AND MEDICAL SYSTEM FOR EXECUTION OF THE METHOD

CROSS REFERENCE TO RELATED APPLICATIONS

This application claims priority of German application No. 10 2010 019 421.2 filed May 5, 2010, which is incorporated by reference herein in its entirety.

FIELD OF THE INVENTION

The invention relates to an imaging method for the representation of results of intravascular imaging (IVB) and CFD results of plaques of a vascular vessel tree of a patient and an imaging medical system for executing the method.

BACKGROUND OF THE INVENTION

In the visualization of the vascular vessel tree, the blood flow, the plaque formation, the plaque structure and further CFD parameters the following standard methods are used:

1. Imaging with 3-D Image Modalities

The 3-D image modalities serve to enable reconstruction of the vascular vessel tree. To this end a contrast medium is injected, in order to strengthen the blood vessels to be observed. The segmentation of the vessels from a 3-D data set represents the vascular lumen, which is used as the input for CFD methods.

2. Intravascular Imaging (IVB)

The intravascular imaging, for example IVUS (Intravascular Ultrasound) or OCT (Optical Coherence Tomography), enables a mapping and analysis of the vessel wall, for example for the representation of plaque. The virtual histology function of IVUS provides automatic means for the detection and classification of plaque, for example the fat content, the fibrousness and the calcification.

3. CFD Method

The simulation of the blood flow by means of the CFD method (Computational Fluid Dynamics) delivers a three-dimensional distribution of the flow parameters, such as for example WSS (Wall Shear Stress), along the surface of the vessel lumen.

3-D image modalities

3-D DSA rotation angiography is a standard method used for the assessment of vascular anatomy before and during interventions. In digital subtraction angiography (DSA), after the creation of mask images, images without contrast medium, and filling images, images with contrast medium, these are subtracted from each other, so that only the temporal changes arising as a result of the contrast medium are obtained, which represent the vessels.

In neuroradiology especially, three-dimensional digital subtraction angiography (3-D DSA) is a routine tool for the planning and execution of minimally invasive procedures. Modem neurological operating theaters integrate this 3-D capability too with a rotating C-arm, in order to enable pre- and intra-procedural 3-D imaging of the cerebral blood vessels.

A C-arm x-ray machine for digital subtraction angiography represented by way of example in FIG. 1 has for example a C-arm 2 rotatably mounted on a stand in the form of a six-axis industrial or articulated-arm robot 1, on the ends of which are attached an x-ray emission source, for example a x-ray emitter 3 with x-ray tube and collimator, and an x-ray image detector 4 as an image acquisition unit.

By means of the articulated-arm robot 1 known, for example, from U.S. Pat. No. 7,500,784 B2, which preferably has six axes of rotation and thus six degrees of freedom, the C-arm 2 can be spatially adjusted at will, for example by being rotated about a center of rotation between the x-ray emitter 3 and the x-ray detector 4. The inventive x-ray system 1 to 4 is in particular rotatable about centers of rotation and axes of rotation in the C-arm plane of the x-ray image detector 4, preferably about the center point of the x-ray image detector 4 and about the axes of rotation bisecting the center point of the x-ray image detector 4.

The known articulated-arm robot 1 has a base frame, which for example is fixedly mounted on a base. Thereupon is fixed a carousel which can be rotated about a first axis of rotation. Arranged pivotably about a second axis of rotation on the carousel is a robot pinion, to which is attached a robot arm, which can be pivoted about a third axis of rotation. On the end of the robot aim is arranged a robot hand, which is rotatable about a fourth axis of rotation. The robot hand has a fixing element for the C-arm 2, which can be pivoted about a fifth axis of rotation and rotated about a sixth axis of rotation running perpendicular thereto.

The realization of the x-ray diagnostic device is not reliant on the industrial robot. Conventional C-arm devices can also be employed here.

The x-ray image detector 4 can be a rectangular or square, flat semiconductor detector, which is preferably created from amorphous silicon (a-Si). Integrating and possibly counting CMOS detectors can, however also be employed.

A patient 6 to be examined as the object under examination is located in the beam path of the x-ray emitter 3 on a patient couch 5, for scanning a heart, for example. Connected to the x-ray diagnostic apparatus is a system control unit 7 with an image system 8, which receives and processes the image signals from the x-ray image detector 4 (operating elements are, for example, not shown). The x-ray images can then be examined on a monitor 9.

Other systems, for example for neuroradiology, use two C-arms. These are so-called biplane systems, as described in greater detail with reference to FIG. 2.

These essentially have two so-called planes, wherein the first plane 10 can comprise the x-ray diagnostic device shown in FIG. 1 with C-arm 2, x-ray emitter 3 and x-ray image detector 4. Via a ceiling bracket 11 a ceiling-hung C-arm 2' with an x-ray emitter 3' and an x-ray image detector 4' of a second plane 12 can be provided. A monitor traffic light 13 with a first display 14 for the first plane 10 and a second display 15 for the second plane 12 can likewise be arranged on the ceiling. A high-voltage generator 16 is provided alongside the system control unit 7.

Intravascular Imaging (IVB)

In order to render the plaque more readily visible, a separate IVUS (Intravascular Ultrasound) catheter can be introduced into the vascular vessel tree of a patient. Such an IVUS system is for example described in DE 198 27 460 A1, from which a method for intravascular ultrasound mapping is known, in which an ultrasound signal transmitter and detector is introduced into a body lumen, and within which this can be moved. The ultrasound signal transmitter and receiver transmits ultrasound signals and captures reflected ultrasound signals, which contain information about the body lumen. A processor coupled to the ultrasound signal transmitter and receiver derives a first image series and a second image series from the captured ultrasound signals, and compares the second image series with the first image series. The processor can also be programmed to monitor the first and second image for cardiovascular periodicity, image quality, temporal change and vessel movement. It can also assign the first image series and the second image series to each other.

For intravascular imaging (IVB), a generally known OCT-catheter (Optical Coherence Tomography) can however also be introduced into the vessel.

CFD method

In DE 10 2008 014 792 B3 a method for the simulation of a blood flow in a vessel section is described, wherein an image acquisition of a vessel area encompassing the vessel section is obtained, a 3-D vessel section model is determined from the image acquisition, a number of blood flow parameters are read in, taking account of the, or of each blood flow parameter, the blood flow in the vessel section model is simulated and a number of hemodynamic parameters are output. It is here provided for that the image acquisition with an implant introduced into the vessel section is obtained in such a way that image data of the implant is included, and that the 3-D vessel section model is determined taking account of the image data of the implant employed. Further, a corresponding device for the simulation of a blood flow in a vessel section is specified.

In today's medical world, the dynamic behavior of the blood flow in an aneurysm is frequently regarded as an important factor for the pathogenesis of the aneurysm, that is for its occurrence and development.

As is known from the article "Image-Based Computational Simulation of Flow Dynamics in a Giant Intracranial Aneurysm" by D. A. Steinman, J. S. Milner, C. J. Morley, S. P. Lowie and D. W. Holdsworth from the American Journal of Neuroradiology (2003), Number 24, pp 559 through 566, a number of so-called hemodynamic parameters are connected with a growth and a rupture of the aneurysm. A hemodynamic parameter is in particular understood to be a parameter relating to hemodynamics, that is the flow dynamics of the blood. As hemodynamic parameters the article cited includes a pressure, a shear stress affecting the vessel wall and a flow rate.

In order to draw conclusions about hemodynamic parameters of this kind, for example, the blood flow in a vessel section, which for example includes the aneurysm, is for example simulated.

To this end, in the aforementioned article "Image-Based Computational Simulation of Flow Dynamic in a Giant Intracranial Aneurysm" a 3-D vessel section model is determined from a 3-D image acquisition, which was obtained by means of a rotation angiography. The blood flow in the 3-D vessel section model is simulated by means of the CFD method. The simulation is here performed assuming rigid vessel walls and a constant blood viscosity. CFD is a method of numeric flow simulation. The model equations used in the numeric flow mechanics are mostly based on a Nervier-Stokes equation, on a Euler or potential equation.

SUMMARY OF THE INVENTION

The object of the invention is to represent the results of intravascular imaging and CFD results of plaques of a vascular vessel tree of a patient, such as for example the plaque formation, the plaque structure and CFD parameters like the wall shear stress, and thus to improve the workflow in a simple manner.

The object is achieved by a method and by a device according to the features specified in the independent claims. Advantageous embodiments are specified in the dependent claims.

According to the invention the object is achieved for a method by the following steps:
  acquisition of a 3-D image data set of the area under examination with x-ray beams for the generation of 3-D x-ray images,
  generation of a 3-D reconstruction image of the area under examination from the 3-D x-ray images,
  generation of IVB images by means of intravascular imaging (IVB),
  identification of larger calcified plaques in the 3-D x-ray images and IVB images for the determining of orientation points or landmarks,
  correlation and/or registration of the spatial position of the plaques on the basis of the orientation points or landmarks and
  merging and reproduction of the IVB image data and 3-D image data.

It is thereby possible in a simple manner to obtain a readily comprehensible representation of results of intravascular imaging and CFD results of plaques of a vascular vessel tree of a patient, such as for example the plaque formation, the plaque structure and CFD parameters such as wall shear stress.

According to the invention a minimizing of the distance of the voxels in the 3-D space can be performed for correlation and/or registration.

It has proved to be advantageous if the function for minimization of the distance of the voxels in the 3-D space takes the following form:

$$\sum_i \sum_j (r_i^{IVB} - r_j^X)^2$$

where $r_i^{IVB}$ or $r_j^X$ respectively determine the coordinates of the $i^{th}$ or $j^{th}$ voxels respectively in the IVB or 3-D x-ray data set.

In an advantageous manner the identification of larger calcified plaques in the 3-D x-ray images and NB images can take place by means of identification of the voxels which contain calcium.

According to the invention the reproduction of the NB image data and 3-D image data can take place by means of color-coded 3-D rendering of CFD results derived from the IVB image data.

It has proved to be advantageous if the reproduction of the IVB image data and 3-D image data takes place based on corresponding cross-sectional information from the intravascular imaging (NB) and/or 3-D x-rays in a multiplanar format.

According to the invention the reproduction can take place in selected positions along the vessel, which for example displays abnormal WSS behavior.

According to the invention the NB images by means of intravascular imaging can take place with intravascular ultrasound (NUS) or optical coherence tomography (OCT).

According to the invention the object is achieved for a device by means of
  a 3-D x-ray machine for the generation of a 3-D image data set,
  an IVB-device for the generation of at least one NB image,
  image storage means for buffering of the 3-D image data set and of the NB image,
  a 3-D image processing stage for the generation of a 3-D reconstruction image from the 3-D image data set and identification of blood vessels in the 3-D reconstruction image, an NB image processing stage for the identification of blood vessels in the NB image, a correlation or registration device for the correlation or registration of the 3-D reconstruction image and of the NB image with the aid of the data from the identification, a fusion device for precise vessel superimposition and a 3-D reproduction device for reproduction of the merged images.

In an advantageous manner the device for generation of an NB image can be an IVUS catheter and the device for generation of an IVB image an OCT catheter.

BRIEF DESCRIPTION OF THE DRAWINGS

The invention is explained in greater detail below on the basis of exemplary embodiments represented in the drawing, wherein:

FIG. 3 shows an inventive arrangement for the representation of images and FIG. 4 shows the inventive method.

DETAILED DESCRIPTION OF THE INVENTION

Figure 1:
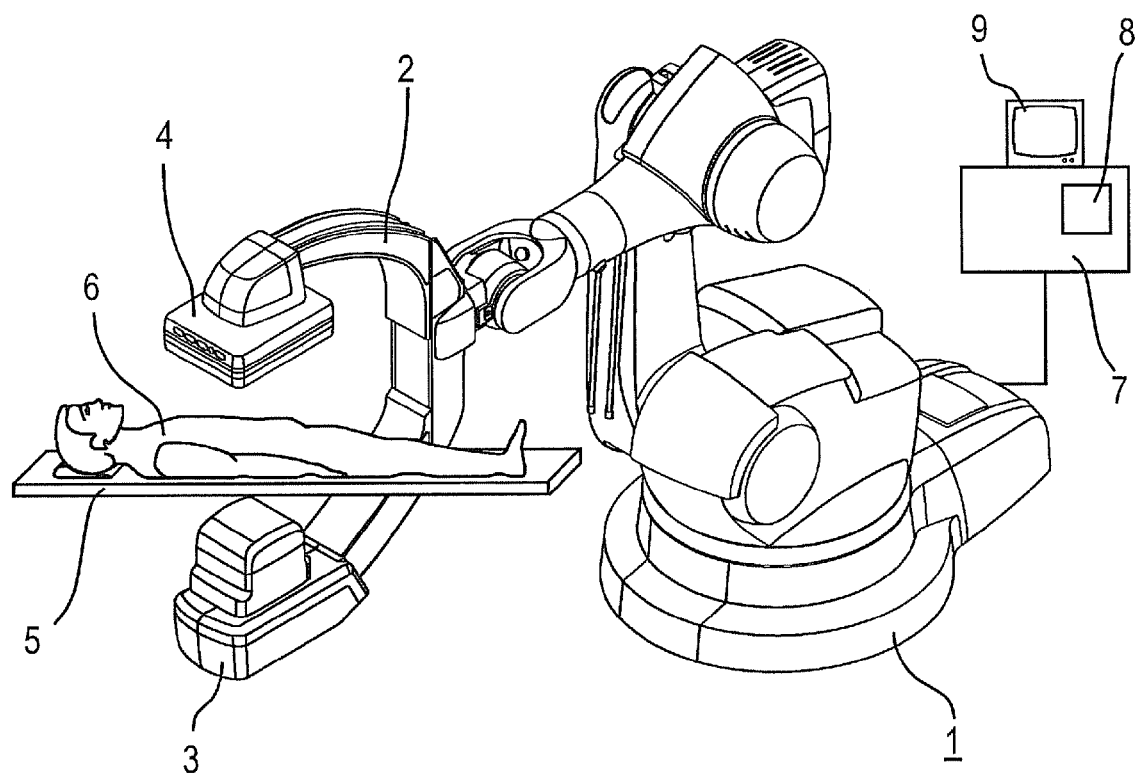
FIG. 1 shows a known x-ray C-arm system for radiology, cardiology or neurosurgery with an industrial robot as the carrier apparatus.
Figure 2:
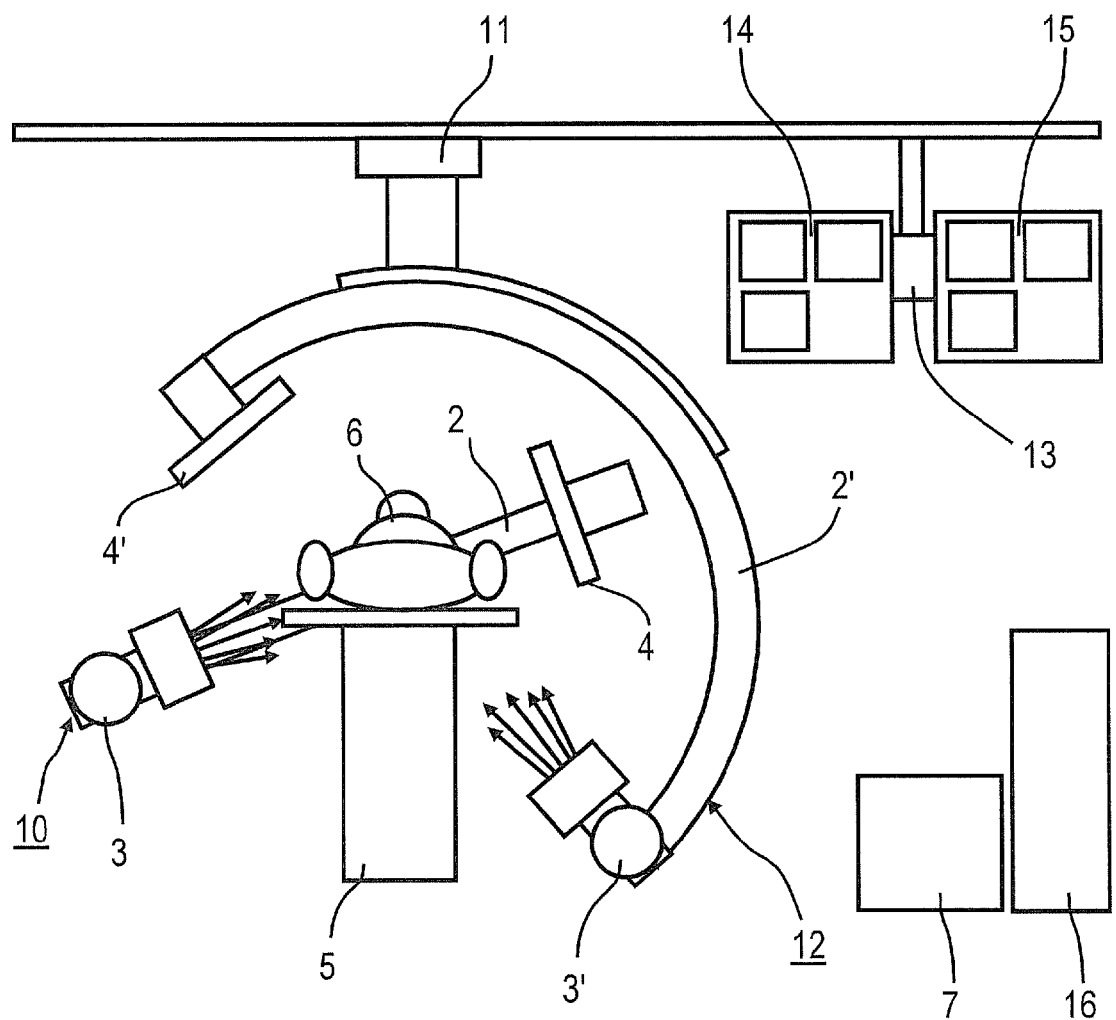
FIG. 2 shows a known biplane C-arm x-ray machine for neuroradiology.
Figure 3:
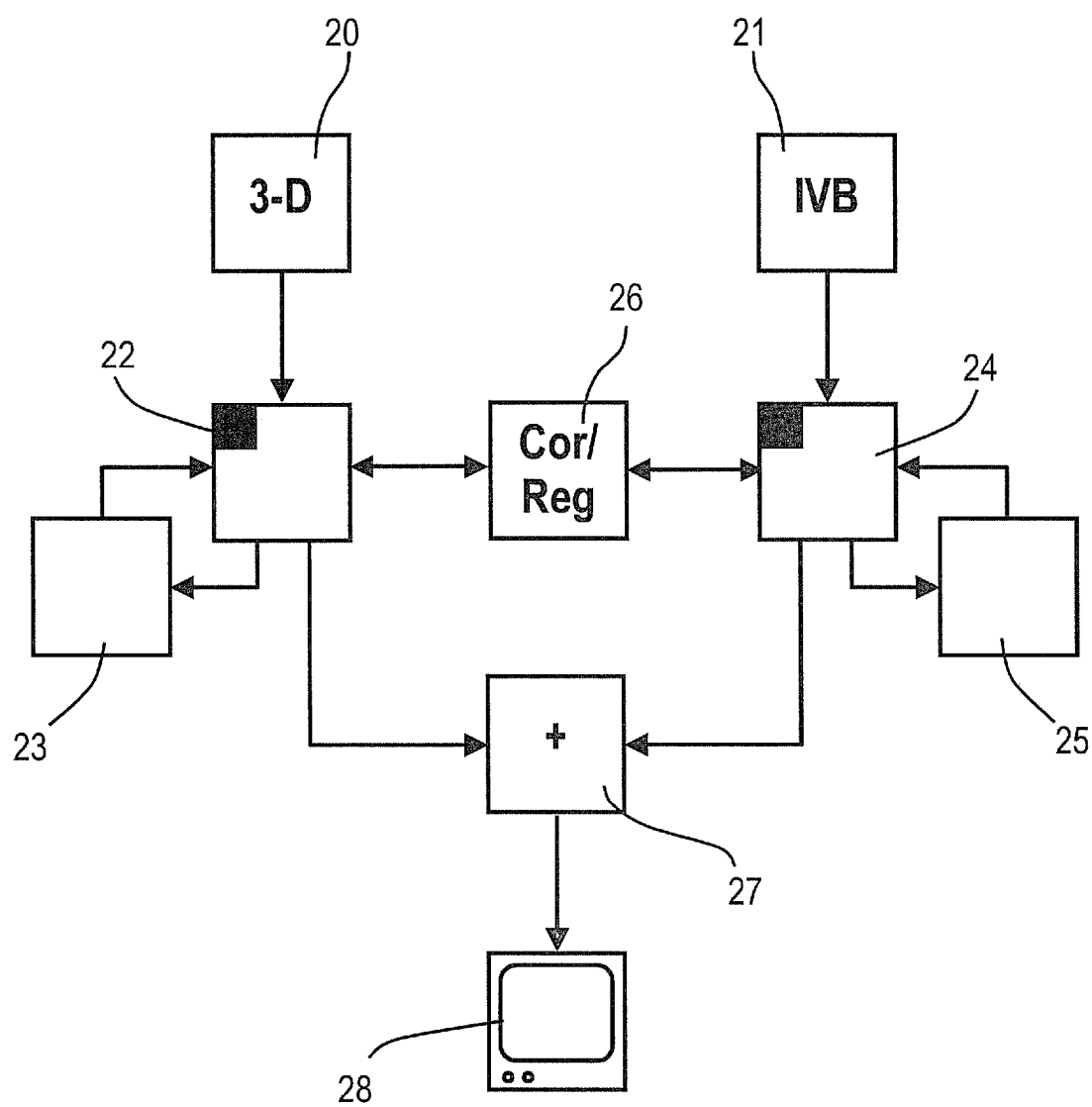

FIG. 3 shows an inventive medical system for the representation of results of intravascular imaging (IVB) and CFD results of plaques of a vascular vessel tree of a patient in conjunction with x-ray angiography with a 3-D x-ray machine 20 and an NB-device 21. Connected to the 3-D x-ray machine 20, for example for rotational angiography such as DynaCT, is a 3-D image memory 22, in which is stored an acquired 3-D image data set, from which after acquisition of the complete 3-D image data set a 3-D reconstruction image is calculated by a 3-D image processing stage 23, which is then likewise stored in the 3-D image memory 22. Subsequently, likewise by means of the 3-D image processing stage 23, the spatial position for example of the larger calcified plaques of the blood vessels in the 3-D reconstruction image, that is the voxels which contain calcium is identified and this data assigned to the 3-D image data set in the 3-D image memory 22.

The NB image of the NB device 21, for example an NUS or an OCT catheter, is buffered in an NB image memory 24. By means of an NB image processing stage 25 the spatial position of the larger calcified plaques of the blood vessels in the NB image, and thus the voxels which contain calcium, are likewise identified, and this data assigned to the current NB image data set in the IVB image memory 24.

By means of a correlation or registration device 26, the 3-D reconstruction image is then registered from the 3-D image memory 22 and the NB image from the NB image memory 24 with the aid of the data from the identification of the larger calcified plaques.

For this the voxels which contain calcium have their distance in the 3-D space minimized. The function for minimization can especially take the following form:

$$\sum_i \sum_j (r_i^{IVB} - r_j^X)^2$$

where $r_i^{IVB}$ or $r_j^X$ respectively determine the coordinates of the $i^{th}$ or $j^{th}$ voxels respectively in the IVB or 3-D x-ray data set.

Subsequently, the thus correlated or registered images are superimposed in a vessel-precise manner by means of a fusion device 27 and the 3-D reconstruction image overlaid with the NB image represented on a 3-D reproduction device 28.

After such a spatial registration with the aid of the calcified orientation points or landmarks, the information can be reproduced in a merged manner in various ways.

One special possibility is the customary color-coded 3-D rendering of the CFD results (WWS). In selected positions along the vessel, which for example displays an abnormal WSS, the corresponding cross-section information from IVUS and/or 3-D x-rays can be reproduced in a multiplanar format, in order to show the composition of the vessel walls.

Alternatively, the 3-D data sets of the vessel tree captured by means of CT angiography with DynaCT can be automatically registered with 2-D angiography and fluoroscopy.

The known registration between 2-D x-rays and IVUS can then be used in order to register CTA (and CFD) with IVUS.

The inventive method procedure is now explained in greater detail on the basis of FIG. 4. Firstly, in step S1), a complete 3-D image data set is acquired with the 3-D x-ray machine 20. In step S2) a 3-D reconstruction image of the area under examination is calculated from the 3-D image data set by means of the 3-D image processing stage 23, from which according to step S3) the spatial position of the larger calcified plaques of the blood vessels, that is to say the calcium-containing voxels, are identified, so that orientation points or landmarks are obtained.

In step S4), at least one IVB image is acquired with the NB-device 21, which can be for example an IVUS or an OCT catheter. According to step S5) the spatial position of the larger calcified plaques of the blood vessels is identified from the IVB image for the determining of orientation points or landmarks, so that it is possible to define the voxels containing calcium.

According to step S6) a correlation and/or registration of the spatial position of the plaques takes place based on the orientation points or landmarks in the 3-D reconstruction images and NB images by means of the correlation or registration device 26 with the aid of a minimization of the distance of the defined voxels in the 3-D space.

Finally, the 3-D reconstruction images and NB images correlated or registered on the basis of the orientation points or landmarks are merged on a precise vessel basis in step S7) by means of the fusion device 27 and the 3-D reconstruction image data merged with the NB-image data represented on the 3-D reproduction device 28 according to step S8).

The basic idea of the present invention is to obtain a correlation between the plaque formation, the plaque structure and CFD parameters, for example the wall shear stress.

An approximation procedure, in order for example to correlate IVUS images and CFD results, is as follows:

For 3-D imaging with x-ray beams, the calcified plaque on the wall can be seen and detected, in the event where manual annotation may be necessary.

In principle the proposed method identifies the larger calcified plaques from NUS and 3-D x-ray data and correlates or registers their spatial position. For this the voxels which contain calcium are identified and their distance in the 3-D space minimized. The function for minimization can especially take the following form:

$$\sum_i \sum_j (r_i^{IVUS} - r_j^X)^2$$

where $r_i^{IVUS}$ or $r_j^X$ respectively determines the coordinates of the or voxels respectively in the IVUS or 3-D x-ray data set. After such a spatial registration with the aid of the calcified orientation points or landmarks, various paths can be realized, in order to represent the information in a merged manner.

One special possibility is the customary color-coded 3-D rendering of the CFD results (WWS). In selected positions along the vessel, which for example shows an abnormal WSS, the corresponding cross-section information from IVUS and/or 3-D x-rays can be represented in a multiplanar format, in order to show the composition of the vessel walls.

An alternative method of achieving this registration is the capturing of 3-D data sets of the vessel tree by means of rotation angiography, for example DynaCT. The CTA (CT angiography) can then be merged with DynaCT by means of the known 3-D/3-D fusion algorithms. DynaCT is automatically registered with 2-D angiography and fluoroscopy. The known registration between 2-D x-ray images and IVUS images can then be used to register CTA (and CFD) with IVUS.

The invention claimed is:

1. An imaging method for representing a plaque of a vascular vessel tree of a patient, comprising:
    acquiring 3-D x-ray images of an area under examination by a 3-D x-ray imaging device;
    generating a 3-D reconstruction image of the area under examination from the 3-D x-ray images;
    generating an intravascular image of the area under examination by an intravascular imaging device;
    identifying the plaque in the 3-D reconstruction image and the intravascular image and assigning a spatial position of the plaque to the images represented by voxels in 3-D space;
    registering the 3-D reconstruction image with the intravascular image based on the identification;
    fusing the 3-D reconstruction image with the intravascular image; and
    reproducing the fused image for representing the plaque.

2. The method as claimed in claim 1, wherein the registration is performed by minimizing a distance of voxels in a 3-D space.

3. The method as claimed in claim 2, wherein the minimization is performed by the following form:

$$\sum_i \sum_j (r_i^{IVB} - r_j^X)^2$$

where $r_i^{IVB}$ or $r_j^{?X}$ respectively determines coordinates of $i^{th}$ or $i^{th}$ voxels respectively in the intravascular image or the 3-D reconstruction image.

4. The method as claimed in claim 1, wherein the plaque is identified by identifying voxels containing calcium.

5. The method as claimed in claim 1, wherein the plaque is represented by a color-coded 3-D CFD result derived from the intravascular image.

6. The method as claimed in claim 1, wherein the fused image is reproduced based on corresponding cross-section information of the intravascular imaging and the 3-D reconstruction in a multiplanar format.

7. The method as claimed in claim 6, wherein the fused image is reproduced in selected positions along the vascular vessel tree.

8. The method as claimed in claim 7, wherein the selected positions show an abnormal wall shear stress behavior.

9. The method as claimed in claim 1, wherein the intravascular imaging is generated by an intravascular ultrasound or an optical coherence tomography.

10. The method as claimed in claim 1, wherein an orientation point or a landmark of the plaque is determined by the identification.

11. An imaging medical system for representing a plaque of a vascular vessel tree of a patient, comprising:
    a 3-D x-ray imaging device for generating 3-D x-ray images of an area under examination;
    an intravascular imaging device for generating an intravascular image of the area under examination;
    image storage device for buffering the 3-D x-ray images and the intravascular image;
    a 3-D image processing device for generating a 3-D reconstruction image from the 3-D x-ray images and identifying the plaque in the 3-D reconstruction image and assigning a spatial position of the plaque to the 3-D reconstruction image represented by voxels in 3-D space;
    an intravascular image processing device for identifying the plaque in the intravascular image and assigning a spatial position of the plaque to the intravascular image represented by voxels in 3-D space;
    a registration device for registering the 3-D reconstruction image with the intravascular image based on the identification;
    a fusion device for superimposing the 3-D reconstruction image with the intravascular image; and
    a 3-D reproduction device for reproducing the superimposed image.

12. The imaging medical system as claimed in claim 11, wherein the intravascular image is generated by an Intravascular Ultrasound catheter.

13. The imaging medical system as claimed in claim 11, wherein the intravascular image is generated by an Optical Coherence Tomography catheter.

* * * * *